(12) United States Patent
Hansson

(10) Patent No.: US 8,436,139 B2
(45) Date of Patent: May 7, 2013

(54) PEPTIDE-BASED IMMUNIZATION THERAPY FOR TREATMENT OF ATHEROSCLEROSIS

(75) Inventor: Göran K. Hansson, Stockholm (SE)

(73) Assignee: CardioVax, LLC, Torrance, CA (US)

( * ) Notice: Subject to any disclaimer, the term of this patent is extended or adjusted under 35 U.S.C. 154(b) by 991 days.

(21) Appl. No.: 11/373,682

(22) Filed: Mar. 10, 2006

(65) Prior Publication Data

US 2006/0233817 A1    Oct. 19, 2006

Related U.S. Application Data

(63) Continuation of application No. PCT/SE2004/001239, filed on Aug. 30, 2004.

(30) Foreign Application Priority Data

Sep. 11, 2003 (SE) ..................................... 0302422

(51) Int. Cl.
*C07K 14/00* (2006.01)

(52) U.S. Cl.
USPC ..................................... 530/326; 424/184.1

(58) Field of Classification Search .................. 530/326, 530/345; 424/184.1
See application file for complete search history.

(56) References Cited

U.S. PATENT DOCUMENTS

| 6,156,315 | A  | * | 12/2000 | Goldberg et al. | ......... | 424/158.1 |
| 7,527,795 | B2 | * | 5/2009  | Nilsson et al.  | ............. | 424/185.1 |
| 7,528,225 | B2 | * | 5/2009  | Nilsson et al.  | ................ | 530/326 |
| 7,544,360 | B2 | * | 6/2009  | Nilsson et al.  | ............. | 424/185.1 |

FOREIGN PATENT DOCUMENTS

| WO | WO0168119 | 9/2001 |
| WO | WO02080954 | 10/2002 |

OTHER PUBLICATIONS

Palinski (Proc. Natl. Acad. Sci. USA 92:821-825, 1995).*
Singh, Rajeeva (Methods in Enzymology (1995), 251(Biothiols, Part A), 167-73).*
Jocelyn, P., Methods in Enzymology 143, 246-256, 1987.*

* cited by examiner

*Primary Examiner* — David Lukton
(74) *Attorney, Agent, or Firm* — K&L Gates LLP; Louis C. Cullman; Michelle Glasky Bergman

(57) ABSTRACT

The present invention relates to a fragment of apolipoprotein B, for immunization for prophylactic or therapeutic treatment of mammals, including humans, against ischemic cardiovascular diseases, in particular myocardial infarction or stroke, as well as diagnosing the presence or absence of antibodies related to increased or decreased risk of developing ischemic cardiovascular diseases including stroke, using said peptide in an assay, pharmaceutical compositions comprising the peptide. The invention further encompasses a particular peptide sequence aggravating disease, which sequence then can be used for diagnostic assays.

17 Claims, 1 Drawing Sheet

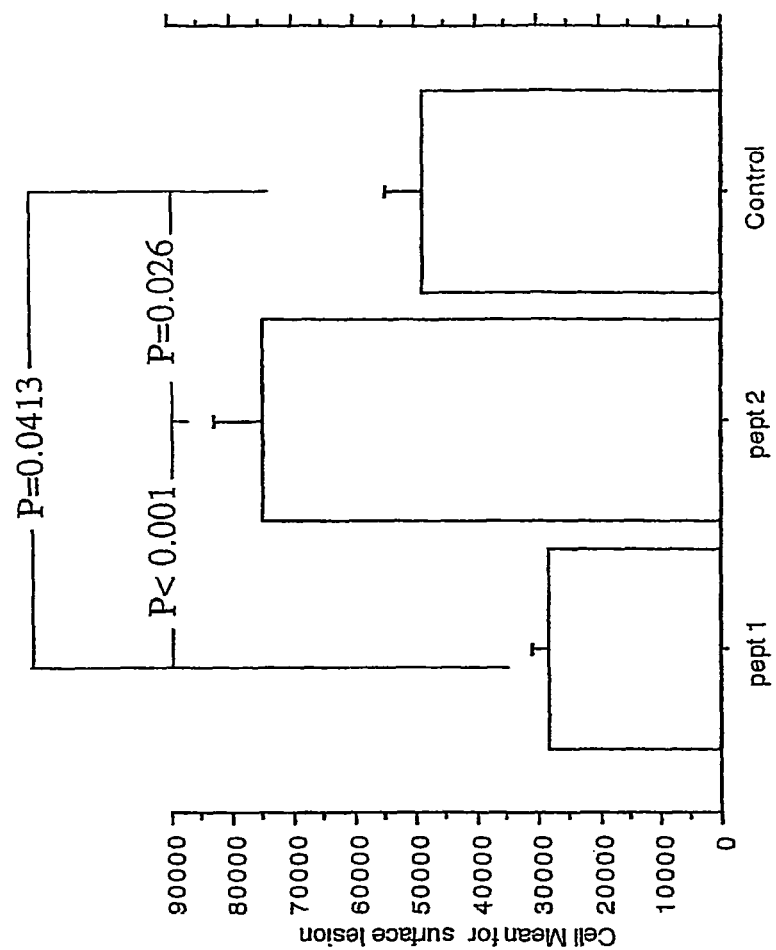

PEPTIDE-BASED IMMUNIZATION THERAPY FOR TREATMENT OF ATHEROSCLEROSIS

This application is a continuation of PCT Application No. PCT/SE2004/001239, filed Aug. 30, 2004, which claims priority to Swedish Application No. 0302422-1, filed on Sep. 11, 2003.

TECHNICAL FIELD

The present invention relates to a new peptide, in particular a peptide to be used for immunization therapy for treatment of atherosclerosis, and for development of peptide based immunochemical assay for the determination of immune response against oxidized low density lipoprotein and the diagnosis of the presence or absence of atherosclerosis.

In particular the invention includes:

1) The use of the peptide of the invention alone, native or MDA-modified, preferably together with a suitable carrier and adjuvant as an immunotherapy or "anti-atherosclerosis "vaccine" for prevention and treatment of ischemic cardiovascular disease.

2) The use of the same peptide in immunochemical assays for detection of antibodies related to increased or decreased risk of development of ischemic cardiovascular diseases.

BACKGROUND

Atherosclerosis is a chronic disease that causes a thickening of the innermost layer (the intima) of large and medium-sized arteries. It decreases blood flow and may cause ischemia and tissue destruction in organs supplied by the affected vessel. Atherosclerosis is the major cause of cardiovascular disease including myocardial infarction, stroke and peripheral artery disease. It is the major cause of death in the Western world and is predicted to become the leading cause of death in the entire world within two decades.

Thus research during the last 20 years has shown that atherosclerosis is an inflammatory disease, which develops at sites of cholesterol accumulation in the artery wall. Specifically, activated T-cells macrophages and antibodies are found in atherosclerotic lesions of humans and experimental animals. A significant proportion of these T cells recognize oxidatively modified LDL (oxLDL). Such cells appear in increased amounts in the circulation of patients undergoing unstable angina and myocardial infarction. Similarly, antibodies to oxLDL can be detected in patient's blood and extracted from plaques. The importance of adaptive immunity for atherosclerosis is further underlined by the finding that severe combined immunodeficiency (SCID) leads to reduced atherosclerosis in hypercholesterolemic mice, while transfer of T cells into such mice increases the extent of the disease.

The LDL particle consists of several different molecules including triglycerides, cholesterol esters, phospholipids, and a large protein, apolipoprotein B100 (apoB). Oxidative modification results in lipid peroxidation, generation of reactive aldehydes, fragmentation of the protein, and binding of aldehydes to amino acid residues of the protein fragments. Antibody responses have been detected to several of these components, including phosphorylcholine and malondialdehyde-modified apoB protein and fragments thereof. Cellular immune responses are likely to be directed against modified protein components since the predominating components of cellular immunity found in lesions are CD4+T cells expressing TCRαβT cell receptors. These cells are known to recognize 15-25 amino acid peptides bound to Major Histocompatability Complex (MHC) class II proteins (e.g., Human Leucocyte Antigen (HLA-DR)) and it is therefore likely that such peptides serve as antigens for the cellular immune response associated with atherosclerosis. It is furthermore likely that we are tolerant to peptides of native apoB and that oxidation breaks tolerance, possibly through formation of aldehyde adducts.

Immunization with oxidized LDL has been shown to reduce atherosclerosis in experimental animals. This observation also suggests the possibility of developing an immune therapy or "vaccine" for treatment of atherosclerosis-based cardiovascular disease in man. One approach to do this would be to immunize an individual with his own LDL after it has been oxidized by exposure to for example copper. However, this approach is complicated by the fact that it is not known which structure in oxidized LDL that is responsible for inducing the protective immunity and if oxidized LDL also may contain epitopes that may give rise to adverse immune reactions.

The identification of epitopes in oxidized LDL is important for several aspects:

First, such epitopes are likely to be responsible for activating the anti-atherogenic immune response observed in animals immunized with oxidized LDL. Peptides containing these epitopes may therefore represent a possibility for development of an immune therapy or "atherosclerosis vaccine" in man. Further, they can be used for therapeutic treatment of atherosclerosis developed in man.

Secondly, peptides containing the identified epitopes can be used to develop ELISAs able to detect antibodies against specific structure in oxidized LDL. Such ELISAs would be more precise and reliable than those presently available using oxidized LDL particles as antigen. It would also allow the analyses of immune responses against different epitopes in oxidized LDL associated with cardiovascular disease.

U.S. Pat. No. 5,972,890 relates to a use of peptides for diagnosing atherosclerosis. The technique presented in said U.S. patent is as a principle a form of radiophysical diagnosis. A peptide sequence is radioactively labelled and is injected into the bloodstream. If this peptide sequence should be identical with sequences present in apoB it will bind to the tissue where there are receptors present for apoB. In vessels this is above all atherosclerotic plaque. The concentration of radioactivity in the wall of the vessel can then be determined e.g., by means of a gamma camera. The technique is thus a radiophysical diagnostic method based on the notion that radioactively labelled peptide sequences will bind to their normal tissue receptors present in atherosclerotic plaque and are detected using an external radioactivity analysis. It is a direct analysis method to identify atherosclerotic plaque. It requires that the patient be given radioactive compounds.

The technique of the present invention is based on quite different principles and methods. In accordance with claim 1 the invention relates to a fragment of apoB for immunisation against cardiovascular disease as well as a method for diagnosing immunological reactions against such a peptide sequence of apoB. Such immune reactions have in turn been found to be increased in individuals who have a developed atherosclerosis. The present technique is based on attaching the peptide sequence in the bottom of polymer wells. When a blood sample is added the peptide will bind antibodies, which are specific to this sequence. The amount of antibodies bound is then determined using an immunological method. In contrast to the technique of said U.S. patent this is thus not a direct determination method to identify and localise atherosclerotic plaque but determines an immunological response, which may show a high degree of co-variation with the extension of the atherosclerosis.

The basic principle of the present invention is thus quite different from that of said patent. The latter depends on binding of a peptide sequence to the normal receptors of the lipoproteins present in atherosclerotic tissue, while the former is based on the discovery of immune reactions against peptide sequence and determination of antibodies to the peptide sequence.

PCT/SE02/00679 discloses a number of peptides for peptide-based immunization therapy of atherosclerosis and development of a peptide-based assay for determination of immune responses against oxidized low density lipoprotein, said peptides being derived from apoB.

Published studies (Palinski et al., 1995, George et al., 1998 and Zhon et al., 2001) have shown that immunisation against oxidised LDL reduces the development of atherosclerosis. This would suggest that immuno reactions against oxidised LDL in general have a protecting effect. Previous results have (PCT/SE02/00679, above), however, surprisingly shown that this is not always the case. Thus in said reference it is shown that using a mixture of peptides #10, 45, 154, 199, and 240 will give rise to an increase of the development of atherosclerosis. Immunisation using other peptide sequences of said reference, e.g., peptide sequences #1, and 30 to 34 lacks total effect on the development of atherosclerosis. The results are surprising because they provide a basis for the fact that immune reactions against oxidised LDL, can protect against the development, contribute to the development of atherosclerosis, and be without any effect at all, depending on which structures in oxidised LDL they are directed to. These findings make it possible to develop immunisation methods, which isolate the activation of protecting immune reactions. Further, they show that immunisation using intact oxidised LDL could have a detrimental effect if the particles used contain a large amount of structures that give rise to atherogenic immuno reactions.

WO 99/08109 relates to the use of a panel of monoclonal mouse antibodies, which bind to particles of oxidised LDL in order to determine the presence of oxidised LDL in serum and plasma. This is thus totally different from the present invention wherein a method for determining antibodies against oxidised LDL is disclosed.

U.S. Pat. No. 4,970,144 relates to a method for preparing antibodies by means of immunisation using peptide sequences, which antibodies can be used for the determination of apolipoproteins using ELISA. This is thus something further quite different from the present invention.

U.S. Pat. No. 5,861,276 describes a recombinant antibody to the normal form of apolipoprotein B. This antibody is used for determining the presence of normal apolipoprotein B in plasma and serum, and for treating atherosclerosis by lowering the amount of particles of normal LDL in the circulation.

Thus in the present invention the use of antibodies are described for treating atherosclerosis. However, contrary to the U.S. Pat. No. 5,861,276, these antibodies are directed to structures present in particles of oxidised LDL and not to the normal particle of LDL. The advantage is that it is the oxidised LDL, which is supposed to give rise to the development of atherosclerosis. The use of antibodies directed to structures being specific to oxidised LDL is not described in said US patent.

SUMMARY OF THE INVENTION

Oxidation of lipoproteins, mainly LDL, in the arterial wall is believed to be an important factor in the development of atherosclerosis. Products generated during oxidation of LDL are toxic to vascular cells, cause inflammation and initiate plaque formation. Epitopes in oxidized LDL are recognized by the immune system and give rise to T cell activation and antibody formation. A bioinformatics approach has been used to identify a peptide derived from LDL, which can elicit a strong cellular immune response. Animal experiments have shown that this peptide, when derivatized with malondialdehyde (MDA) and used for immunization has a protective effect against atherosclerosis.

DETAILED DESCRIPTION OF THE INVENTION

It has thereby been determined that the following peptide, when derivatized with MDA fulfills the criteria required to initiate a cellular immune response. This peptide is $NH_2$-PTVMDFRKFSRNYQLYKSVSLPS-COOH    SEQ. ID. NO. 1 or an active part of this peptide.

The present peptide, SEQ. ID. NO 1, is based on amino acids 625-647 of the amino acid sequence of the human apoB100 protein.

When a peptide synthesized to contain this amino acid sequence is conjugated with MDA and injected into atherosclerosis-prone mice together with a suitable adjuvant, it reduces the development of atherosclerosis in the animals.

The present invention thus relates to a fragment of apoB intended for immunization or therapeutic treatment of mammals, including humans, against ischemic cardiovascular diseases and having immunological prophylactic or therapeutic properties against ischemic cardiovascular diseases, and/or diagnosing the presence or absence of antibodies related to increased or decreased risk of developing ischemic cardiovascular diseases, which fragment is encoded by the peptide sequence $NH_2$-PTVMDFRKFSRNYQLYKSVSLPS-COOH    (SEQ. ID. NO. 1)

or an active part of this peptide.

In accordance with a preferred embodiment the fragment is in native form.

In accordance with a preferred embodiment the fragment is in oxidized form.

In accordance with a preferred embodiment the fragment is a hapten of aldehydes.

In accordance with a preferred embodiment the fragment is modified using MDA or hydroxynonenal.

In accordance with a preferred embodiment the peptide has been oxidized using copper.

In accordance with a preferred embodiment the peptide is present in a combination with phospholipid liposomes.

In accordance with a preferred embodiment the fragment is in the form of a MDA derivative thereof.

In accordance with a preferred embodiment the fragment is in the form of a hydroxynonenal (HNE)-derivative thereof.

A further aspect of the invention relates to the use of the fragment/peptide of above, in native or MDA or HNE derivative form, in the preparation of pharmaceutical compositions intended for immunological prophylactic or therapeutic therapy for the treatment of ischemic cardiovascular diseases, optionally in combination with an adjuvant. In this respect stroke is included as a diagnosis as well as stroke has an ischemic stroke depends on an atherosclerosis with thrombosis in feeding arteries.

In accordance with a preferred embodiment thereof an immunization dose is 0.001 to 400 mg of the fragment/peptide.

Another further aspect of the invention relates to a pharmaceutical preparation comprising a therapeutically effective amount of one or more of the fragment/peptide of above, optionally in combination with one or more pharmaceutically innocuous fillers, and/or adjuvants.

In accordance with a preferred embodiment thereof Freund's complete and/or incomplete adjuvant is used in combination with the fragment/peptide.

In accordance with a preferred embodiment thereof the fragment/peptide is present as linked to cationized bovine serum albumin, and using aluminium hydroxide as an adjuvant.

In accordance with a preferred embodiment thereof the composition is present as an injectable composition.

A particular aspect is a vaccine for immunization of mammals, including humans, against ischemic cardiovascular diseases including stroke comprising the fragment/peptide of above, optionally in combination with an adjuvant.

In accordance with a preferred embodiment thereof Freund's complete and/or incomplete adjuvant is used.

In accordance with a preferred embodiment the vaccine for immunization of mammals, including humans, against ischemic cardiovascular diseases comprising a therapeutically effective amount of purified or recombinantly produced antibodies against the said native and/or MDA and/or HNE modified sequence of above.

In accordance with a preferred embodiment the fragment/peptide present for immunization are present as linked to cationized bovine serum albumin, and using aluminium hydroxide as an adjuvant.

A further aspect of the invention relates to a method of prophylactic or therapeutic treatment of a mammal, including a human being, suffering from atherosclerosis or facing the risk of developing ischemic cardiovascular diseases including stroke, whereby a therapeutically effective amount of the fragment of above, either in native form or in the form of a malone dealdehyde or a hydroxynoneal derivative, is administered to said mammal suffering from atherosclerosis, or facing the risk of developing ischemic cardiovascular diseases, in particular myocardial infarction.

In accordance with a preferred embodiment the method of prophylactic or therapeutic treatment of a mammal, including a human being, suffering from atherosclerosis or facing the risk of developing ischemic cardiovascular diseases, whereby a therapeutically effective amount of one or more of purified, or recombinantly produced antibodies against native and MDA-modified sequence to produce a passive immunization is administered.

In accordance with a preferred embodiment the conditions are one or more of unstable atherosclerotic plaques in which oxidized LDL is likely to contribute to inflammation, cell toxicity and risk for plaque rupture, as well as coronary heart disease in older individuals.

Another aspect of the invention relates to a method of diagnosing the presence or absence of antibodies related to increased or decreased risk of developing ischemic cardiovascular diseases, using the fragment of above in an assay.

In accordance with a preferred embodiment the assay is an immunoassay.

In accordance with a preferred embodiment the immunoassay is an ELISA, RIA, and/or Western blotting.

A further aspect hereof is a method of diagnosing the presence or absence of T cells related to increased or decreased risk of developing ischemic cardiovascular diseases, using the fragment of above in an assay.

In accordance with a preferred embodiment the assay is an immunoassay.

In accordance with a preferred embodiment the immunoassay is a flow cytometry, ELISPOT amd/or ELISA.

In accordance with a preferred embodiment the immunoassay is a flow cytometric analysis that employs the peptide of above bound to an oligomeric complex of recombinant HLA protein.

The present invention further includes the strategy to identify peptide of SEQ. ID. NO. 1. It is based on bioinformatics and a step-wise approach in accordance with the following.

1. The human apo B100 protein sequence is analyzed for amino acid sequences (20-25-mers) that contain motifs permitting binding to the appropriate MHC class II protein. For this purpose, the "share-ware" program, SYFPEITHI, (Biomedical Institute, Heidelberg, Germany) is used.
2. Among sequences obtained through this procedure, those are selected that contains at least one Lysine residue positioned between the anchor motifs for MHC class II binding.
3. Among sequences obtained by means of 1+2, those are selected that contain similarities with other proteins known to be strong immunogens.
4. Among those obtained by means of 1+2+3, the amino acid sequence(s) that shows the strongest homology between man and mouse is selected for immunization.

Another aspect of the invention identifies a peptide that aggravates atherosclerosis when injected into animals together with adjuvant. This peptide is derived from human apoB100, has an amino acid sequence defined below and is modified with MDA.

```
NH2-YSKVHNGSEILFSYFQDLVIT-COOH    SEQ. ID. NO. 2
``` which corresponds to amino acid sequence 4232-4252 of human apoB100. This peptide was chosen as a control based on the criteria described above and is one basis for an diagnostic tool used in an immunoassay, e.g, an ELISA to diagnose the absence/presence of atherosclerotic disease. The peptide of SEQ. ID. NO. 2 is thus linked to more severe disease conditions.

EXPERIMENTAL

Procedure

It was hypothesized that the induction of protective immunity could depend on presentation of peptides derived from apoB100 and modified by adduct formation during oxidative modification of the LDL particle. Further, it was hypothesized that such peptides must have a sequence that (i) contains side chains susceptible to adduct formation, and (ii) permits them to bind to MHC class II molecules. The apoB100 sequence was analyzed to identify such motifs. An amino acid sequence was selected which fulfills them and exhibited minimal differences between man and mouse. A peptide containing this sequence was synthesized and used for immunization of apoE−/− mice. The effect on atherosclerosis was quantified by measuring the size of atherosclerotic lesions after 12 weeks.

Material And Methods/Results

Bioinformatics

Human apolipoprotein B100 (accession number AAA51750) was retrieved from GenBank using Entrez-Protein (National Library of Medicine, Wash. D.C.) search engine.

The full-length sequence was analyzed for H2-Ab binding motifs by using the SYFPEITHI program (Biomedical Institute, Heidelberg, Germany). Among sequences obtained through this method, those containing lysine residues amenable to aldehyde binding in positions between the H2-Ab anchor motifs were selected. The set of peptides thus obtained was subjected to a homology search using Entrez-Protein, and peptide was selected which displayed significant homology between human and murine apoB100. This peptide sequence was denoted peptide SEQ. ID. NO. 1, and used for immunization. As a control, a peptide sequence from the SYFPEITHI search was used which contained a lysine residue in a similar position as for peptide SEQ. ID. NO. 1, displayed homology to the immune associated protein, CRP, but did not display substantial homology between mouse and man. This peptide was denoted SEQ. ID. NO. 2.

Animals 8 week old female apoE−/− mice (B6, Apoe−/−, M&B, Ry, Denmark) were immunized with 100 µg of peptide SEQ. ID. NO. 1, and SEQ. ID. NO. 2, respectively, emulsified with Freund's complete adjuvant to a total volume of 50 µl. Mice were boosted after 2 and 4 weeks with 50 µg of peptide in Freund's incomplete adjuvant. A third group of mice consisting of age-matched male mice was injected according to the same scheme with phosphate-buffered saline (PBS) in adjuvant. 4 weeks after the last boost, mice were anesthetized with carbon dioxide and killed by exsanguination after cardiac puncture. After vascular perfusion with sterile RNase-free PBS, the heart and proximal aorta were removed, embedded in OCT compound, frozen and cryosectioned.

Quantitative analysis of atherosclerosis

The size of atherosclerotic lesions in the proximal aorta was quantified by using Leica Qwin software (for details of the method, see Nicoletti et al., J. Clin. Invest. (1998)) Results were expressed as $\mu m^2$ average lesion area per cross-section, as well as relative lesion area, i.e., lesion area ($\mu m^2$) divided by total aortic cross-section area ($\mu m^2$). The Mann-Whitney U test used for for comparisons between means.

Results

Amino acids 625-647 of the human apoB100 protein were identified as having a suitable sequence for immunization. The criteria are described above. Peptide SEQ. ID. NO. 1 contains the precise sequence of this part of the apoB100 protein. As a control, amino acids 4232-4252, SEQ. ID. NO. 2, were selected, as well, based on the criteria described above.

NH$_2$-PTVMDFRKFSRNYQLYKSVSLPS-COOH   SEQ. ID. NO. 1

NH$_2$-YSKVHNGSEILFSYFQDLVIT-COOH    SEQ. ID. NO. 2 were synthesized by FMOC chemistry and used for immunization as described.

Mice immunized with peptide SEQ. ID. NO. 1 had significantly smaller lesions than control mice injected with PBS/adjuvant alone (FIG. 1). Similarly, lesions in mice immunized with peptide SEQ. ID. NO. 1 were significantly smaller than in mice immunized with peptide SEQ. ID. NO. 2 (FIG. 1). The reduction in lesion size in mice immunized with peptide SEQ. ID. NO. 1 was 42% compared to PBS controls ($p<0.05$) and 62% compared with peptide SEQ. ID. NO. 2 immunized mice ($p<0.001$). Interestingly, lesions in mice immunized with peptide SEQ. ID. NO. 2 were 36% larger than PBS controls ($p<0.05$), implying that peptide SEQ. ID. NO. 2 induces an immune response that aggravates atherosclerosis.

The peptide sequence represents a target for immune reactions that may be of importance for the development of atherosclerosis and ischemic cardiovascular diseases. This peptide may therefore be used to develop immunoassays to determine the association between immune responses (antibody levels, cellular immune responses) against a defined amino acid sequence of oxidized or MDA-modified LDL and the risk for development of cardiovascular disease.

The present peptide also represents a possible mediator of the protective immunity observed in experimental animals immunized with oxidized LDL and may be used for testing in further development of an immunization therapy or "vaccine" against atherosclerosis.

It has now been demonstrated that immunization with the MDA-modified peptide of a sequence derived from apoB100 (SEQ. ID. NO. 1) results in an inhibition of atherosclerosis in experimental animals. The mechanisms through which these athero-protective immune responses operate remain to be fully elucidated. However, it is likely that they involve formation of antibodies to this peptide. Such antibodies could, for example, facilitate the removal of oxidatively damaged LDL particles by macrophage Fc receptors. In line with this, our previous transfer of B cells from animals with high-titer antibodies to MDA-LDL reduces atherosclerosis in apoE null mice (Caligiuri et al., J. Clin. Invest (2002)). Similarly, a repeated injection of immunoglobulins also reduces disease in this animal model of human disease.

It is likely that the atheroprotective immune response may involve induction of antigen-specific T cells that act to dampen vascular inflammation. (Recent studies by the present inventor, point to an important role for T cells producing anti-inflammatory cytokines as inhibitors of atherosclerosis. (Caligiuri et al, Mol Med 2003; Robertson et al, submitted, 2003)).

Macrophage scavenger receptors only recognize LDL with extensive oxidative damage. Recent studies have identified the existence of circulating oxidized LDL. These particles have only minimal oxidative damage and are not recognized by scavenger receptors. Binding of antibodies to these circulating oxidized LDL particles may help to remove them from the circulation before they accumulate in the vascular tissue.

As discussed above antibodies against MDA-modified peptide sequence of the invention in apo B-100 may be generated by active immunization using a synthetic peptide. This procedure requires at least 2-3 weeks before effects are obtained on antibodies and cellular immune responses.

In some situations a more rapid effect may be needed. One example may be unstable atherosclerotic plaques in which oxidized LDL is likely to contribute to inflammation, cell toxicity and risk for plaque rupture. Under these circumstances a passive immunization by injection of purified, or recombinantly produced antibodies against native and MDA-modified sequence may have a more rapid effect.

Another situation in which a passive immunization by injection of purified, or recombinantly produced antibodies may be effective is coronary heart disease in older individuals. Studies have shown that a decrease in antibodies against apo B peptide sequences occurs with increasing age in man and is associated with an increase in the plasma level of oxidized LDL. This may suggest a senescence of the immune cells responsible for producing antibodies against antigens in oxidized LDL and result in a defective clearance of oxidatively damaged LDL particles from the circulation. Accordingly, these subjects would benefit more from a passive immunization by injection of purified, or recombinantly produced antibodies than from an active immunization with apo B-100 peptide sequences.

Although the precise molecular mechanism to explain why peptide immunization reduced atherosclerosis and/or modulate plaque phenotype remains unclear, the novelty of this invention is the concept of using a certain peptide of LDL as immunogen and its feasibility as an immunomodulation strategy. This peptide-based immunization strategy modulates atherosclerotic plaques development. Immunization using homologous oxLDL or native LDL as antigen had been shown to reduce plaque size, however, the availability, production, infectious contamination and safety of homologous human LDL make this approach unappealing for clinical application. Here it is demonstrated that it is feasible to carry out immunotherapy by using synthetic peptides rather than heterogeneous lipoproteins.

In summary, it is demonstrated a novel peptide-based immunomodulatory approach to modulate the growth of atherosclerotic plaques. Although the change in atherosclerosis formation in our model was only 42%, yet this peptide-based immunization may provide an alternative tool in studying, preventing or treating atherosclerosis. Assay models for antibody detection include any immunoassay detecting an antibody, such as ELISA, radioactive immunoassay, Western blotting, as well as detection of antibodies bound to peptides, and other methods for analysis.

Assays for atheroprotective T cells include quantitation of such cells by immunostaining followed by flow cytometry. To identify T cell subsets with atheroprotective capacity, it will be appropriate to use combinations of fluorescent antibodies that recognize cell type specific surface proteins. In order to identify antigen-specific T cells it will be necessary to use tetramers or similar preparations containing recombinant HLA molecules to which the antigenic peptide SEQ. ID. NO. 1 (or related peptides) has been fused by cDNA technology. Finally, antigen-specific T cell responses can be quantitated by short term incubation with antigenic peptide (SEQ. ID. NO. 1 or related peptides) followed by counting of T cells that express an established activation marker (IL-2, CD69, IL-2R, or similar). This can be done either by flow cytometry, ELISPOT or ELISA of spent culture media.

Administration of the peptide is normally carried out by injection, such as subcutaneous injection, intravenous injection, intramuscular injection or intraperitoneal injection. A first immunizing dosage can be 0.001 to 400 mg per patient depending on body weight, age, and other physical and medical conditions. In particular situations a local administration of a solution containing the peptide via catheter to the coronary vessels is possible as well. Oral preparations may be contemplated as well, although particular precautions must be taken to admit absorption into the blood stream. Further nasal inhalation formulations may be contemplated, as well. An injection dosage may contain 0.5 to 99.5% by weight of the fragment or peptide of the present invention.

The peptide is normally administered as such or may be linked to cationized bovine serum albumin, and using aluminium hydroxide or Freund's complete and incomplete adjuvants as an adjuvant. Other adjuvants known in the art can be used as well.

The peptide can also be used as therapeutic agent in patients already suffering from an atherosclerosis. Thus any suitable administration route can be used for adding the peptide of the invention.

FIGURE LEGENDS

FIG. 1 shows lesion response to the different peptides in accordance with the present invention.

The invention claimed is:

1. A peptide consisting of the amino acid sequence NH2-PTVMDFRKFSRNYQLYKSVSLPS-COOH (SEQ ID NO: 1).

2. A peptide of the amino acid sequence NH2-PTVMDFRKFSRNYQLYKSVSLPS-COOH (SEQ ID NO: 1) wherein the peptide has been modified using malondialdehyde or hydroxynonenal, or oxidized, and wherein the peptide has no more than 23 amino acids.

3. A peptide of the amino acid sequence NH2-PTVMDFRKFSRNYQLYKSVSLPS-COOH (SEQ ID NO: 1) wherein the peptide is a hapten of aldehydes, and wherein the peptide has no more than 23 amino acids.

4. A peptide according to claim 2, wherein the peptide has been modified using malondialdehyde or hydroxynonenal.

5. A peptide according to claim 2 wherein the peptide has been oxidized using copper.

6. A peptide according to claim 2, in form of a malondialdehyde (MDA) derivative thereof.

7. A pharmaceutical preparation comprising a peptide according to either of claim 1 or claim 2, wherein the peptide is linked to cationized bovine serum albumin, and in combination with an aluminium hydroxide adjuvant.

8. A peptide according to claim 2, in form of a hydroxynonenal-derivative thereof.

9. A vaccine for immunization of mammals, including humans, against ischemic cardiovascular diseases comprising the peptide of either of claim 1 or claim 2, wherein the peptide is linked to cationized bovine serum albumin in combination with an aluminium hydroxide adjuvant.

10. A vaccine for immunization of mammals, including humans, against ischemic cardiovascular diseases comprising the peptide of either of claim 1 or claim 2, in combination with an adjuvant.

11. A vaccine according to claim 10, wherein the adjuvant comprises Freund's complete and/or incomplete adjuvant.

12. A pharmaceutical preparation comprising a peptide according to either of claim 1 or claim 2, in combination with one or more pharmaceutically innocuous fillers, and/or adjuvants.

13. The pharmaceutical composition according to claim 12, wherein the peptide is in a combination with phospholipid liposomes.

14. A pharmaceutical composition according to claim 12, wherein the adjuvant is Freund's complete and/or incomplete adjuvant.

15. A pharmaceutical composition according to claim 12, wherein the composition is an injectable composition.

16. A method of treating a cardiovascular disease comprising administering a therapeutically effective amount of the pharmaceutical preparation of claim 12, wherein the cardiovascular disease is one or more of unstable atherosclerotic plaques in which oxidized LDL is likely to contribute to inflammation, cell toxicity, or risk for plaque rupture.

17. A method of treating atherosclerosis comprising administering a therapeutically effective amount of the pharmaceutical preparation of claim 12 and wherein the atherosclerosis is treated as a result of said administration.

* * * * *

```
SEQUENCE LISTING

<160> NUMBER OF SEQ ID NOS: 2

<210> SEQ ID NO 1
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Pro Thr Val Met Asp Phe Arg Lys Phe Ser Arg Asn Tyr Gln Leu Tyr
 1               5                  10                  15

Lys Ser Val Ser Leu Pro Ser
            20

<210> SEQ ID NO 2
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Tyr Ser Lys Val His Asn Gly Ser Glu Ile Leu Phe Ser Tyr Phe Gln
 1               5                  10                  15

Asp Leu Val Ile Thr
            20
```